US00PP22704P2

(12) United States Plant Patent
Isobe et al.

(10) Patent No.: US PP22,704 P2
(45) Date of Patent: May 1, 2012

(54) ***PETUNIA* PLANT NAMED 'SUNSURFCOPAKA'**

(50) Latin Name: *Petunia×hybrida*
Varietal Denomination: Sunsurfcopaka

(75) Inventors: Yasuko Isobe, Shiga (JP); Takeshi Kanaya, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 273 days.

(21) Appl. No.: 12/658,052

(22) Filed: Feb. 1, 2010

(51) Int. Cl.
*A01H 5/00* (2006.01)

(52) U.S. Cl. ..... Plt./356.23

(58) Field of Classification Search ..... Plt./356.1, Plt./356.23
See application file for complete search history.

(56) References Cited

OTHER PUBLICATIONS

UPOV ROM GTITM Computer Database, GTI JOUVE Retrieval Software 2011/10 Citation for 'Sunsurfcopaka'.*

* cited by examiner

*Primary Examiner* — Wendy C Haas
(74) *Attorney, Agent, or Firm* — C. A. Whealy

(57) ABSTRACT

A new and distinct cultivar of *Petunia* plant named 'Sunsurfcopaka', characterized by its compact and mounding plant habit; vigorous growth habit; freely branching and flowering plant habit; long flowering period; medium-sized red-colored flowers; and good garden performance.

1 Drawing Sheet

Botanical designation: *Petunia×hybrida.*
Cultivar denomination: 'SUNSURFCOPAKA'.

BACKGROUND OF THE INVENTION

The present invention relates to a new and distinct cultivar of *Petunia* plant, botanically known as *Petunia×hybrida* and hereinafter referred to by the name 'Sunsurfcopaka'.

The new *Petunia* plant is a product of a planned breeding program conducted by the Inventors in Higashiomi, Shiga, Japan. The objective of the breeding program is to create new compact and mounding *Petunia* plants with freely branching habit and attractive flower coloration.

The new *Petunia* plant originated from a cross-pollination made by the Inventors in April, 2005 in Higashiomi, Shiga, Japan of a proprietary selection of *Petunia×hybrida* identified as code number Px287-1, not patented, as the female, or seed, parent with a proprietary selection of *Petunia×hybrida* identified as code number Px612-1, not patented, as the male, or pollen, parent. The new *Petunia* plant was discovered and selected by the Inventors as a single flowering plant within the progeny of the stated cross-pollination in a controlled environment in Higashiomi, Shiga, Japan in September, 2006.

Asexual reproduction of the new *Petunia* plant by terminal cuttings in a controlled environment in Higashiomi, Shiga, Japan since October, 2006, has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Sunsurfcopaka'. These characteristics in combination distinguish 'Sunsurfcopaka' as a new and distinct cultivar of *Petunia:*

1. Compact and mounding plant habit.
2. Vigorous growth habit.
3. Freely branching and flowering plant habit.
4. Long flowering period.
5. Medium-sized red-colored flowers.
6. Good garden performance.

Plants of the new *Petunia* can be compared to plants of the female parent selection. Plants of the new *Petunia* differ primarily from plants of the female parent selection in flower color as plants of the female parent selection have red purple-colored flowers.

Plants of the new *Petunia* can be compared to plants of the male parent selection. Plants of the new *Petunia* differ primarily from plants of the male parent selection in the following characteristics:

1. Plants of the new *Petunia* have smaller flowers than plants of the male parent selection.
2. Plants of the new *Petunia* and the male parent selection differ in flower color as plants of the male parent selection have pink-colored flowers.

Plants of the new *Petunia* can also be compared to plants of the *Petunia* 'Sunremi', disclosed in U.S. Plant Pat. No. 16,803. In side-by-side comparisons conducted in Higashiomi, Shiga, Japan, plants of the new *Petunia* and 'Sunremi' differed primarily in the following characteristics:

1. Plants of the new *Petunia* were more compact than and not as broad as plants of 'Sunremi'.
2. Plants of the new *Petunia* were more mounding than and not as upright and outwardly spreading as plants of 'Sunremi'.
3. Plants of the new *Petunia* had smaller and lighter green-colored leaves than plants of 'Sunremi'.

4. Plants of the new *Petunia* had smaller flowers than plants of 'Sunremi'.

BRIEF DESCRIPTION OF THE PHOTOGRAPHS

The accompanying colored photographs illustrate the overall appearance of the new *Petunia* plant, showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunsurfcopaka' grown in a container.

The photograph at the bottom of the sheet is a close-up view of typical flowers of 'Sunsurfcopaka'.

DETAILED BOTANICAL DESCRIPTION

The aforementioned photographs and following observations, measurements and values describe plants grown in 15-cm containers in Higashiomi, Shiga, Japan, under commercial practice during the late spring and early summer in an outdoor nursery with day temperatures averaging 23° C. and night temperatures averaging 13° C. Plants were four months old when the photographs and description were taken. In the following description, color references are made to The Royal Horticultural Society Colour Chart, 2001 Edition, except where general terms of ordinary dictionary significance are used.

Botanical classification: *Petunia×hybrida* 'Sunsurfcopaka'.

Parentage:

*Female, or seed, parent*.—Proprietary selection of *Petunia×hybrida* identified as code number Px287-1, not patented.

*Male, or pollen, parent*.—Proprietary selection of *Petunia×hybrida* identified as code number Px612-1, not patented.

Propagation:

*Type*.—By terminal cuttings.

*Time to initiate roots*.—About one week at temperatures of 15° C. to 20° C.

*Time to produce a rooted young plant*.—About three weeks at temperatures of 15° C. to 20° C.

*Root description*.—Fibrous; white in color.

*Rooting habit*.—Freely branching.

Plant description:

*Plant and growth habit*.—Compact and mounding plant habit; freely branching habit with numerous lateral branches developing per plant; pinching enhances lateral branch development; vigorous growth habit.

*Plant height*.—About 16.5 cm.

*Plant diameter*.—About 26.8 cm.

Lateral branch description:

*Length*.—About 13.2 cm.

*Diameter*.—About 2.5 mm.

*Internode length*.—About 1.3 cm.

*Strength*.—Strong, flexible.

*Aspect*.—Upright to outwardly.

*Texture*.—Pubescent.

*Color*.—Close to 144A.

Foliage description:

*Arrangement*.—Alternate, simple.

*Length*.—About 3.6 cm.

*Width*.—About 1.6 cm.

*Shape*.—Ovate.

*Apex*.—Broadly acute.

*Base*.—Cuneate.

*Margin*.—Entire.

*Texture, upper and lower surfaces*.—Pubescent.

*Venation pattern*.—Pinnate; reticulate.

*Color*.—Developing and fully expanded leaves, upper surface: Close to 137D; venation, close to 144B. Developing and fully expanded leaves, lower surface: Close to 144A; venation, close to 144B.

*Petioles*.—Length: About 7 mm. Diameter: About 2.2 mm. Texture, upper and lower surfaces: Pubescent. Color, upper and lower surfaces: Close to 144B.

Flower description:

*Flower arrangement and habit*.—Single salverform flowers arising from leaf axils; freely flowering habit with usually about 31 open flowers per plant; flowers face upright to outwardly.

*Fragrance*.—None detected.

*Natural flowering season*.—Early flowering habit, plants of the new *Petunia* initiate and develop flowers about three to four weeks after planting; long flowering period; flowering commences naturally during the spring and plants flower continuously throughout the summer until late autumn in Japan.

*Flower longevity*.—Individual flowers last about seven to ten days on the plant; flowers not persistent.

*Flower diameter*.—About 4.2 cm.

*Flower length (depth)*.—About 4.3 cm.

*Throat diameter*.—About 11.6 mm.

*Tube diameter, base*.—About 3 mm.

*Tube length*.—About 2.7 cm.

*Flower bud*.—Shape: Cylindrical. Length: About 3.7 cm. Diameter: About 7.6 mm. Color: Close to 182B.

*Corolla*.—Arrangement: Five petals fused at the base and opening into a flared trumpet. Petal length from throat: About 1.4 cm. Petal width: About 2 cm. Petal shape: Spatulate. Petal apex: Rounded to cuspidate. Petal margin: Entire. Petal texture, upper and lower surfaces: Smooth, glabrous. Throat texture: Smooth, glabrous. Tube texture: Pubescent. Color: Petal, when opening, upper surface: Close to 45A. Petal, when opening, lower surface: Close to 186D. Petal, fully opened, upper surface: Close to 45B; venation, close to 45B. Petal, fully opened, lower surface: Close to 186D; venation, close to 186D. Throat: Close to 173D; venation, close to 178A. Tube: Close to 176B.

*Calyx*.—Arrangement: One star-shaped calyx tube with five sepals fused at the base per flower. Sepal length: About 1.2 cm to 1.4 cm. Sepal width: About 1.9 mm. Sepal shape: Lanceolate. Sepal apex: Obtuse. Sepal margin: Entire. Sepal texture, upper and lower surfaces: Pubescent. Color, upper surface: Close to 137B. Color, lower surface: Close to 137C.

*Peduncles*.—Length: About 3 cm. Diameter: About 1.4 mm. Strength: Strong. Texture: Pubescent. Color: Close to 144A.

*Reproductive organs*.—Stamens: Quantity/arrangement: Five per flower. Stamen length: About 1.7 cm to 2 cm. Anther shape: Ellipsoidal. Anther size: About 2.1 mm by 2.4 mm. Anther color: Close to 11C. Pollen amount: Moderate. Pollen color: Close to 11D. Pistils: Quantity: One per flower. Pistil length: About 2.1 cm. Style color: Close to 145C. Stigma shape: Transversely ellipsoidal. Stigma color: Close to 143B.

Ovary color: Close to 144A. Seeds/fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen/pest resistance: Plants of the new *Petunia* have not been observed to be resistant to pathogens and pests common to *Petunia* plants.

It is claimed:

1. A new and distinct *Petunia* plant named 'Sunsurfcopaka' as illustrated and described.

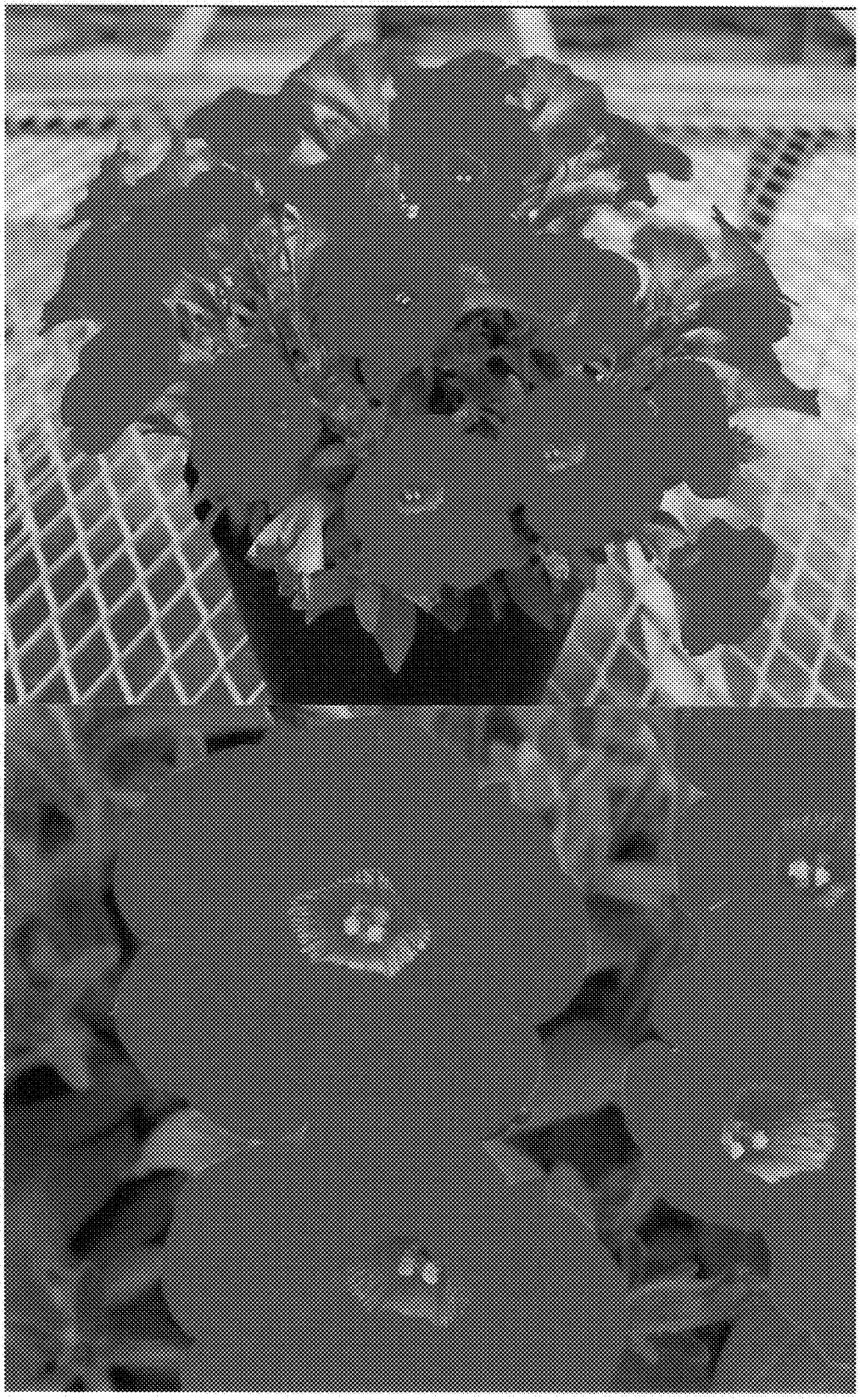

* * * * *